United States Patent [19]

Griffiths et al.

[11] Patent Number: 5,684,157
[45] Date of Patent: Nov. 4, 1997

[54] PROCESS FOR THE PREPARATION OF OPTIONALLY 2-SUBSTITUTED 5-CHLOROIMIDAZOLE-4-CARBALDEHYDES

[75] Inventors: Gareth Griffiths, Visp; Gerhard Stucky, Brig-Glis, both of Switzerland

[73] Assignee: Lonza Ltd., Gampel/Valais, Switzerland

[21] Appl. No.: 783,205

[22] Filed: Jan. 14, 1997

Related U.S. Application Data

[62] Division of Ser. No. 644,249, May 10, 1996.

[30] Foreign Application Priority Data

May 17, 1995 [SZ] Swaziland ................. 1451/95

[51] Int. Cl.⁶ .................................................. C07D 233/68
[52] U.S. Cl. .................................................. 548/335.5
[58] Field of Search .................................... 548/335.5

[56] References Cited

U.S. PATENT DOCUMENTS

| | | |
|---|---|---|
| 4,345,935 | 8/1982 | Thibault. |
| 4,355,040 | 10/1982 | Furukawa et al. ............. 548/336 |
| 5,395,943 | 3/1995 | Yamamoto et al.. |
| 5,442,076 | 8/1995 | Gosteli et al.. |
| 5,486,617 | 1/1996 | Griffiths et al.. |
| 5,508,425 | 4/1996 | Griffiths et al. ............. 548/343.1 |
| 5,565,577 | 10/1996 | Mokhallalati et al.. |

FOREIGN PATENT DOCUMENTS

| | | |
|---|---|---|
| 0579212 | 1/1994 | European Pat. Off.. |
| 0614890 | 9/1994 | European Pat. Off.. |
| 0614892 | 9/1994 | European Pat. Off.. |
| 0653422 | 5/1995 | European Pat. Off.. |
| 2804435 | 8/1978 | Germany. |

*Primary Examiner*—Patricia L. Morris
*Attorney, Agent, or Firm*—Fisher, Christen & Sabol

[57] ABSTRACT

A process for the preparation of 2-substituted 5-chloroimidazole-4-carbaldehydes of the general formula:

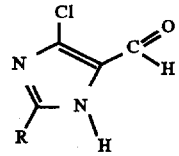

wherein R is hydrogen, an alkyl group, an alkenyl group, a cycloalkyl group, a benzl group or a phenyl group. The imidazole compounds are important starting products for the preparation of hypotensive pharmaceuticals or herbicides.

5 Claims, No Drawings

PROCESS FOR THE PREPARATION OF OPTIONALLY 2-SUBSTITUTED 5-CHLOROIMIDAZOLE-4-CARBALDEHYDES

This is a divisional application of Ser. No. 08/644,249, filed on May 10, 1996.

BACKGROUND OF THE INVENTION

1. Field of the Invention

The invention involves a novel process for the preparation of 2-substituted 5-chloroimidazole-4-carbaldehydes of the general formula:

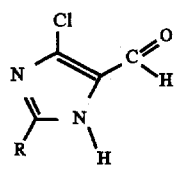
I in which R denotes hydrogen, an alkyl group, an alkenyl group, a cycloalkyl group, a benzyl group or a phenyl group.

2. Background Art

A number of ways are known for the preparation of the compounds according to general formula I.

Thus, U.S. Pat. No. 4,355,040 describes a process by which 2-amino-3,3-dichloroacrylonitrile is reacted with an aldehyde to give the corresponding azomethine intermediate, which is further reacted with a hydrogen halide and water to give the 2-substituted 5-haloimidazole-4-carbaldehyde. There are no experimental data given in the patent. A great disadvantage of the synthesis is that the 2-amino-3,3-dichloroacrylonitrile used must first be prepared starting from dichloroacetonitrile, by its reaction with hydrogen cyanide/sodium cyanide. The extremely toxic reactants an the safety precautions associated therewith, which are necessary even for the preparation of the starting product, make the overall process industrially unsuitable.

U.S. Pat. No. 4,355,040 discloses, in a further variant, a 3-stage process, in which, in a first stage, an amidine hydrochloride is cyclized with dihydroxyacetone at high $NH_3$ pressure, the imidazole alcohol is halogenated and is finally oxidized to the aldehyde. It was shown that pressures of greater than 20 bar are necessary for the ring-closure reaction.

The oxidation of the alcohol functions, according to U.S. Pat. No. 4,355,040, in the presence of chromium oxide. It is obvious that oxidation with heavy metal oxides, which are generally not able to be recirculated, is no longer justifiable from current ecological viewpoints.

Broad Description of the Invention

The main object of the invention is to provide a process which does not have the above-described disadvantages of the prior art. Other objects and advantages of the invention are set out herein or are obvious herefrom to one skilled in the art.

The process and intermediate compounds of the invention achieve the objects and advantages of the invention.

The invention involves a process for the preparation of optionally 2-substituted 5-chloroimidazole-4-carbaldehydes of the general formula:

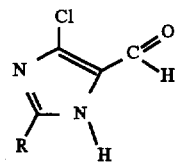
I in which R denotes hydrogen, an alkyl group, an alkenyl group, a cycloalkyl group, a benzyl group or a phenyl group. The process includes reacting an optionally 2-substituted 5-chloroimidazole of the general formula:

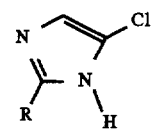
II in which R has the above-described meaning, with an amine of the general formula:

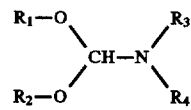
III in which $R_1$ and $R_2$ are identical or different and denote a $(C_1-C_6)$-alkyl group or $R_1$ and $R_2$ together form a $(C_2-C_3)$-alkylene bridge, $R_3$ and $R_4$ are identical or different and denote a $(C_1-C_6)$-alkyl group or $R_2$ and $R_4$ together with the amine nitrogen form a 5- or 6-membered saturated heterocycle, which may contain oxygen or nitrogen as an additional hetero atom, to give an optionally 2-substituted 5-chloroimidazol-4-ylidenemethylamine of the general formula:

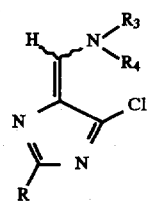
IV in which R, $R_3$ and $R_4$ have the above-described meanings. Finally, the amine of general formula IV is hydrolyzed to give the end product.

Preferably, the invention process is carded out in the presence of a tertiary amine as a base. Preferably, the 2-substituted 5-chloroimidazol-4-ylidenemethylamine of general formula IV is not isolated before it is hydrolyzed. Preferably, the reaction with the amine of general formula III is carried out at a temperature between 20° and 200° C. in the presence of an inert solvent.

The invention also involves 2-substituted 5-chloroimidazol-4-ylidenemethylamines of the general formula:

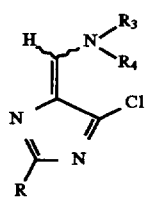
IV in which R, $R_3$ and $R_4$ have the above-described meanings. Preferably, the amine of general formula IV is (2-n-butyl-5-chloroimidazol-4-ylidenemethyl)-dimethylamine, or (2-n- butyl-5-chloroimidazol-4-ylidenemethyl)diethylamine, or (2-n-propyl-5-chloroimidazol-4-ylidenemethyl) dimethylamine, or (2-n-propyl-5-chloroimidazol-4-ylidenemethyl)diethylamine.

The 2-substituted 5-chloroimidazole-4-carbaldehydes of general formula I are important starting products for the preparation of hypotensive pharmaceuticals (U.S. Pat. No. 4,355,040) or of herbicidally active compounds (DE-A 2804435).

DETAILED DESCRIPTION OF THE INVENTION

According to the invention, an optionally 2-substituted 5-chloroimidazole of the general formula:

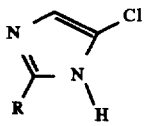     II in which R has the above-described meaning, is first reacted with an amine of the general formula:

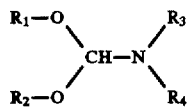     III in which $R_1$ and $R_2$ are identical or different and denote a $(C_1-C_6)$-alkyl group or $R_1$ and $R_2$ together form a $(C_2-C_3)$-alkylene bridge, $R_3$ and $R_4$ are identical or different and denote a $(C_1-C_6)$-alkyl group or $R_2$ and $R_4$ together with the amine nitrogen form a 5- or 6-membered saturated heterocycle, which may contain oxygen or nitrogen as an additional hetero atom, to give an optionally 2-substituted 5-chloroimidazol-4-ylidenemethylamine of the general formula:

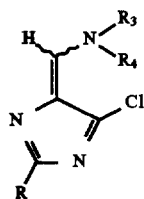     IV in which R, $R_3$ and $R_4$ have the above-described meaning. The amine of general formula IV is then hydrolyzed to provide the end product of the general formula II.

R in the meaning of alkyl represents straight-chain or branched $C_1-C_5$-alkyl, such as, methyl, ethyl, propyl, isopropyl, n-butyl, sec-butyl, tert-butyl, pentyl and its isomers or hexyl and its isomers. A preferred alkyl for R is n-propyl or n-butyl. R in the meaning of alkenyl represents straight-chain or branched $C_1-C_6$-alkenyl, such as, 1-propenyl, 2-propenyl, 1-butenyl, 2-butenyl, 3-butenyl, pentenyl and its isomers or hexenyl and its isomers. A preferred alkenyl for R is 2- or 3- butenyl. Representatives of cycloalkyl are cyclopropyl, cyclobutyl, cyclopentyl, and cyclohexyl. Both benzyl and phenyl can carry substituents, such as, halo, nitro, amino and said alkyls.

The term halogen (halo) is expediently understood to include fluorine (fluoro), chlorine (chloro), bromine (bromo) and iodine (iodo), preferably chlorine (chloro).

The 2-substituted 5-chloroimidazole of general formula II as a starting compound for the process of the invention is accessible by chlorination of the corresponding 3,5-dihydroimidazol-4-one according to European Published Patent Application No. A 0,614,890.

Suitable amines of general formula II are those in which $R_1$ and $R_2$ have the identical meaning and denote $C_1-C_6$-alkyl, such as, methyl, ethyl, propyl, isopropyl, n-butyl, sec-butyl, tert-butyl, pentyl and its isomers or hexyl and its isomers, or in which $R_1$ and $R_2$ together form an ethylene bridge and in which $R_3$ and $R_4$ have the identical meaning and represent one of the said $C_1-C_6$-alkyl groups.

$R_3$ and $R_4$ together with the amine nitrogen can also form a 5- or 6-membered saturated heterocycle, which can contain oxygen or nitrogen as an additional hetero atom. Therefore, $R_3$ and $R_4$ together with the amine nitrogen can form a pyrrolidine ring, a piperazine ring, a piperidine ring or a morpholine ring. Preferably, $R_1$, $R_2$, $R_3$ and $R_4$ represent methyl or ethyl.

Particularly suitable amines of general formula III are dimethoxymethyldimethylamine and diethoxymethyldiethylamine.

The amines of general formula III are expediently used in an amount of 1 to 5 molar equivalents, preferably 1 to 2 molar equivalents, based on 1 mol of 2-substituted 5-chloroimidazole of general formula II.

A selective reaction to give the optionally 2-substituted 5-chloroimidazole-4-ylidenemethylamine of general formula IV can be achieved if the procedure is carded out in the presence of a tertiary amine as a base. Expediently, the tertiary amine is employed in an amount of 0.05 to 2.0 molar equivalents, based on I mol of the 2-substituted 5-chloroimidazole of general formula 11. Preferably, a trialkylamine, such as, triethylamine, is used. The reaction with the amine of general formula III expediently proceeds at a temperature between 20° and 200° C., preferably at a temperature of 100° to 150° C., in the presence of an inert solvent. Although lower temperatures are possible, they retard the reaction and promote side reactions. Suitable solvents which have proved useful are higher-boiling aromatics, such as, chlorobenzene or toluene.

The resulting optionally 2-substituted 5-chloroimidazol-4-ylidenemethylamines of general formula IV are not disclosed in the literature and form an essential constituent of the invention as a central intermediate of the process of the invention. Particularly preferred compounds of general formula IV are (2-butyl-5-chloroimidazol-4-ylidenemethyl) dimethylamine (R is n-butyl, and each of $R_3$ and $R_4$ is methyl), (2-butyl-5-chloroimidazol-4-ylidenemethyl) diethylamine (R is n-butyl, and each of $R_3$ and $R_4$ is ethyl), (2-n-propyl-5-chloroimidazol-4-ylidenemethyl) dimethylamine (R is n-propyl, and each of $R_3$ and $R_4$ is methyl) and (2-n-propyl-5-chloroimidazol-4-ylidenemethyl) diethylamine (R is n-propyl, and each of $R_3$ and $R_4$ is ethyl).

Generally, the compounds of general formula IV are not isolated in the course of the process, but are directly hydrolyzed to give the end product.

The hydrolysis conditions are not critical, that is the hydrolysis can proceed in acidic, alkaline or neutral conditions.

The resulting 2-substituted 5-chloroimidazole-4-carbaldehyde can be isolated in a manner conventional for those skilled in the art, generally by extraction from the aqueous reaction mixture with a suitable solvent.

Example 1

(a) Preparation of (2-n-butyl-5-chloroimidazol-4-ylidenemethyl) dimethylamine

A solution of 2-n-butyl-5-chloro-1H-imidazole (0.79 g, 5 mmol) and dimethoxymethyldimethylamine (0.80 g, approximately 92 percent pure, 6.2 mmol) in chlorobenzene (20 ml) was heated for 1.5 hours at 130° C. 10 ml of the reaction solution was evaporated to dryness and dried under high vacuum. The dark-brown oil (0.46 g) thusly obtained contained the title compound (approximately 80 percent pure according to H-NMR); this corresponded to a yield of approximately 70 percent, based on the starting 2-n-butyl-5-chloro-1H-imidazole. Data concerning the product is:

$^1$H-NMR (400 MHz, CDCl$_3$); δ 0.92 (3H, t), 1.42 (2H, m), 1.74 (2H, m), 2.71 (2H, t), 3.36 (3H, s), 3.80 (3H, s), 7.37 (1H, s).

MS; 213 (M$^+$), 171 (M-42)(100%).

(b) Preparation Of (5-chloro-2-propylimidazol-4-ylidenemethyl) dimethylamine

A solution of 5-chloro-2-propyl-1H-imidazole (0.72 g, 5 mmol), dimethoxymethyldimethylamine (0.77 g, approximately 92 percent pure, 6 mmol) and triethylamine (0.10 g, 1 mmol) in chlorobenzene (25 ml) was heated for 1 hour at 60° C. and for 2 hours under reflux. Removing the solvent in a rotavapor gave the title compound in virtually quantitative yield. Data concerning the product was:

$^1$H-NMR (400 MHz, CDCl$_3$); δ 0.96 (3H, t), 1.78 (2H, m), 2.60 (2H, t), 3.39 (3H, s), 3.80 (3H, s), 7.38 (1H, s).

MS; 199 (M$^+$), 171 (M-28)(100%).

Example 2

(a) Preparation of 2-n-butyl-5-Chloroimidazole-4-Carbaldehyde (Solvent: Chlorobenzene)

A solution of 2-n-butyl-5-chloro-1H-imidazole (1.59 g, 10 mmol), dimethoxymethyldimethylamine (1.94 g, approximately 92 percent pure, 15 mmol) and triethylamine (0.10 g, 1.0 mmol) in chlorobenzene (44 ml) was heated for 2.5 hours at 130° C., cooled to 30% and poured into 2N HCl (50 ml). The mixture was stirred for 0.5 hour at room temperature and was adjusted from pH −0.34 to pH 1.20 by addition of 30 percent strength sodium hydroxide solution (8.9 ml). The phases were separated and the aqueous phase was extracted twice, each time with 30 ml of ethyl acetate. The combined organic phases were dried (MgSO$_4$), filtered, concentrated and dried at high vacuum. The solid (1.67 g) thusly obtained contained the title compound (approximately 75 percent pure according to H-NMR); this corresponded to a yield of approximately 67 percent, based on the starting 2-n-butyl-5-chloro-1H-imidazole. Other data concerning the product was:

$^1$H-NMR (400 MHz, CDCl$_3$); δ 0.93 (3H, t), 1.42 (2H, m), 1.75 (2H, m), 2.82 (2H, t), 9.61 (1H, s), 11.38 (1H, br. s).

b) Preparation of 2-n-butyl-5-Chloroimidazole-4-Carbaldehyde (Solvent: Toluene)

A solution of 2-n-butyl-5-chloro-1H-imidazole (1.59 g, 10 mmol), dimethoxymethyldimethylamine (1.94 g, approximately 92 percent pure, 15 mmol) and triethylamine (0.10 g, 1.0 mmol) in toluene (35 ml) was heated for 4.5 hours at 110° C., cooled to 30° C. and poured into 2N HCl (50 ml). The mixture was stirred for 0.5 hour at room temperature and was adjusted from pH −0.28 to pH 1.20 by addition of 30 percent strength sodium hydroxide solution (8.7 ml). The phases were separated and the aqueous phase was extracted twice, each time with 30 ml of ethyl acetate. The combined organic phases were dried (MgSO$_4$), filtered, concentrated and dried at high vacuum. The solid (1.64 g) thusly obtained contained the title compound (approximately 80 percent pure according to H-NMR); this corresponded to a yield of approximately 70 percent, based on the starting 2-n-butyl-5-chloro-1H-imidazole.

(c) Preparation of 2-Propyl-5-Chloroimidazole-4-Carbaldehyde

A solution of 5-chloro-2-propyl-1H-imidazole (1.45 g, 10 mmol), dimethoxymethyldimethylamine (1.55 g. approximately 92 percent pure, 12 mmol) and triethylamine (0.10 g, 1 mmol) in chlorobenzene (50 ml) was heated for 1 hour at 80% and 2.5 hours under reflux, cooled to room temperature and poured into 2M hydrochloric acid (100 ml). The pH was adjusted to pH 1.97 by addition of 30 percent strength sodium hydroxide solution (19 ml) and the mixture was extracted three times, each time with 50 ml of ethyl acetate. The combined organic phases were dried and concentrated on a rotavapor. The yield of the product was 1.27 g (approximately 90 percent pure according to H-NMR), 66 percent based on 5-chloro-2-propyl-1H-imidazole. Other data concerning the product was:

$^1$H-NMR (400 MHz, CDCl$_3$); δ 1.01 (3H, t), 1.84 (2H, m), 2.83 (2H, t), 9.64 (1H, s), 11.56 (b. s, 1H).

What is claimed is:

1. A 2-substituted 5-chloroimidazol-4-ylidenemethylamine of the formula:

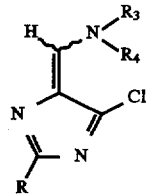

IV wherein R is hydrogen, alkyl, alkenyl, cycloalkyl, benzyl or phenyl, and R$_3$ and R$_4$ are identical or different and each is (C$_1$–C$_6$)-alkyl.

2. (2-n-Butyl-5-chloroimidazol-4-ylidenemethyl) dimethylamine.

3. (2-n-Butyl-5-chloroimidazol-4-ylidenemethyl) diethylamine.

4. (2-n-Propyl-5-chloroimidazol-4-ylidenemethyl) dimethylamine.

5. (2-n-Propyl-5-chloroimidazol-4-ylidenemethyl) diethylamine.

* * * * *

UNITED STATES PATENT AND TRADEMARK OFFICE
CERTIFICATE OF CORRECTION

PATENT NO. : 5,684,157
DATED : November 4, 1997
INVENTOR(S) : Griffiths et al.

It is certified that error appears in the above-indentified patent and that said Letters Patent is hereby corrected as shown below:

Title page, under the heading

[30] Foreign Application Priority Data
    delete"[SZ] Swaziland" and insert --[CH] Switzerland--.

Signed and Sealed this

Thirteenth Day of January, 1998

Attest:

BRUCE LEHMAN

Attesting Officer      Commissioner of Patents and Trademarks